(12) United States Patent
Cook

(10) Patent No.: US 8,014,614 B2
(45) Date of Patent: Sep. 6, 2011

(54) METHOD AND SYSTEM FOR COMPRESSING DATA

(75) Inventor: Michael Joseph Cook, Oconomowoc, WI (US)

(73) Assignee: General Electric Company, Schenectady, NY (US)

( * ) Notice: Subject to any disclaimer, the term of this patent is extended or adjusted under 35 U.S.C. 154(b) by 814 days.

(21) Appl. No.: 12/102,546

(22) Filed: Apr. 14, 2008

(65) Prior Publication Data

US 2009/0257633 A1    Oct. 15, 2009

(51) Int. Cl.
*G06K 9/36* (2006.01)
(52) U.S. Cl. .................. 382/232; 382/233; 382/131
(58) Field of Classification Search .................. 382/232, 382/233, 131; 438/437; 257/E21.235, E21.538
See application file for complete search history.

(56) References Cited

U.S. PATENT DOCUMENTS

| | | | |
|---|---|---|---|
| 6,269,193 | B1 | 7/2001 | Young et al. |
| 6,912,319 | B1 | 6/2005 | Barnes et al. |
| 7,050,639 | B1 | 5/2006 | Barnes et al. |
| 2002/0057844 | A1 | 5/2002 | Sirohey |
| 2004/0136602 | A1 | 7/2004 | Nagaraj et al. |
| 2007/0278409 | A1 | 12/2007 | Cook et al. |

*Primary Examiner* — Anh Hong Do
(74) *Attorney, Agent, or Firm* — Dean Small; The Small Patent Law Group

(57) ABSTRACT

A method for compressing imaging data includes acquiring a stream of imaging data, and dividing the stream of imaging data into a plurality of interstices, each interstice including a plurality of detected events. The also includes classifying the detected events within each interstice based on a probability of occurrence of the detected event, and reordering the detected events within each interstice based on the probability of occurrence to compress the image data. The method further includes generating a ring pair identification number for each detected event in the plurality of interstices.

20 Claims, 12 Drawing Sheets

Table 2

| Ring# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | Ring# |
|---|---|---|---|---|---|---|---|---|---|---|---|---|---|---|---|---|---|---|---|---|---|---|---|---|---|
| | | | | | | | | | | | | | | | | | | | | | | | | | Crystal 1 |
| 1 | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 1 |
| 2 | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 2 |
| 3 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 3 |
| 4 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 4 |
| 5 | 96 | 97 | 98 | 99 | 100 | 101 | 102 | 103 | 104 | 105 | 106 | 107 | 108 | 109 | 110 | 111 | 112 | 113 | 114 | 115 | 116 | 117 | 118 | 119 | 5 |
| 6 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 6 |
| 7 | 144 | 145 | 146 | 147 | 148 | 149 | 150 | 151 | 152 | 153 | 154 | 155 | 156 | 157 | 158 | 159 | 160 | 161 | 162 | 163 | 164 | 165 | 166 | 167 | 7 |
| 8 | 168 | 169 | 170 | 171 | 172 | 173 | 174 | 175 | 176 | 177 | 178 | 179 | 180 | 181 | 182 | 183 | 184 | 185 | 186 | 187 | 188 | 189 | 190 | 191 | 8 |
| 9 | 192 | 193 | 194 | 195 | 196 | 197 | 198 | 199 | 200 | 201 | 202 | 203 | 204 | 205 | 206 | 207 | 208 | 209 | 210 | 211 | 212 | 213 | 214 | 215 | 9 |
| 10 | 216 | 217 | 218 | 219 | 220 | 221 | 222 | 223 | 224 | 225 | 226 | 227 | 228 | 229 | 230 | 231 | 232 | 233 | 234 | 235 | 236 | 237 | 238 | 239 | 10 |
| 11 | 240 | 241 | 242 | 243 | 244 | 245 | 246 | 247 | 248 | 249 | 250 | 251 | 252 | 253 | 254 | 255 | 256 | 257 | 258 | 259 | 260 | 261 | 262 | 263 | 11 |
| 12 | 264 | 265 | 266 | 267 | 268 | 269 | 270 | 271 | 272 | 273 | 274 | 275 | 276 | 277 | 278 | 279 | 280 | 281 | 282 | 283 | 284 | 285 | 286 | 287 | 12 |
| 13 | 288 | 289 | 290 | 291 | 292 | 293 | 294 | 295 | 296 | 297 | 298 | 299 | 300 | 301 | 302 | 303 | 304 | 305 | 306 | 307 | 308 | 309 | 310 | 311 | 13 |
| 14 | 312 | 313 | 314 | 315 | 316 | 317 | 318 | 319 | 320 | 321 | 322 | 323 | 324 | 325 | 326 | 327 | 328 | 329 | 330 | 331 | 332 | 333 | 334 | 335 | 14 |
| 15 | 336 | 337 | 338 | 339 | 340 | 341 | 342 | 343 | 344 | 345 | 346 | 347 | 348 | 349 | 350 | 351 | 352 | 353 | 354 | 355 | 356 | 357 | 358 | 359 | 15 |
| 16 | 360 | 361 | 362 | 363 | 364 | 365 | 366 | 367 | 368 | 369 | 370 | 371 | 372 | 373 | 374 | 375 | 376 | 377 | 378 | 379 | 380 | 381 | 382 | 383 | 16 |
| 17 | 384 | 385 | 386 | 387 | 388 | 389 | 390 | 391 | 392 | 393 | 394 | 395 | 396 | 397 | 398 | 399 | 400 | 401 | 402 | 403 | 404 | 405 | 406 | 407 | 17 |
| 18 | 408 | 409 | 410 | 411 | 412 | 413 | 414 | 415 | 416 | 417 | 418 | 419 | 420 | 421 | 422 | 423 | 424 | 425 | 426 | 427 | 428 | 429 | 430 | 431 | 18 |
| 19 | 432 | 433 | 434 | 435 | 436 | 437 | 438 | 439 | 440 | 441 | 442 | 443 | 444 | 445 | 446 | 447 | 448 | 449 | 450 | 451 | 452 | 453 | 454 | 455 | 19 |
| 20 | 456 | 457 | 458 | 459 | 460 | 461 | 462 | 463 | 464 | 465 | 466 | 467 | 468 | 469 | 470 | 471 | 472 | 473 | 474 | 475 | 476 | 477 | 478 | 479 | 20 |
| 21 | 480 | 481 | 482 | 483 | 484 | 485 | 486 | 487 | 488 | 489 | 490 | 491 | 492 | 493 | 494 | 495 | 496 | 497 | 498 | 499 | 500 | 501 | 502 | 503 | 21 |
| 22 | 504 | 505 | 506 | 507 | 508 | 509 | 510 | 511 | 512 | 513 | 514 | 515 | 516 | 517 | 518 | 519 | 520 | 521 | 522 | 523 | 524 | 525 | 526 | 527 | 22 |
| 23 | 528 | 529 | 530 | 531 | 532 | 533 | 534 | 535 | 536 | 537 | 538 | 539 | 540 | 541 | 542 | 543 | 544 | 545 | 546 | 547 | 548 | 549 | 550 | 551 | 23 |
| 24 | 552 | 553 | 554 | 555 | 556 | 557 | 558 | 559 | 560 | 561 | 562 | 563 | 564 | 565 | 566 | 567 | 568 | 569 | 570 | 571 | 572 | 573 | 574 | 575 | 24 |
| Crystal 2 | | | | | | | | | | | | | | | | | | | | | | | | | |

FIG. 8

| Hypothetical Intermediate Table of Events Per RingPair ID | |
|---|---|
| RingPair ID | Num Events |
| 0 | 0 |
| 1 | 2 |
| 2 | 1 |
| 3 | 0 |
| 4 | 0 |
| 5 | 4 |
| 6 | 0 |
| ... | ... |
| 600 (Last RingPair ID) | 1 |

| Corresponding "Hypothetical" Ordered I_EVENTS List | | | | |
|---|---|---|---|---|
| hiTraxID | hiTraxID<128 | dtFanPairID | dtFanPairID<8192 | Type |
| 44 | Y | 17791 | N | B |
| 283 | N | 9635 | N | B |
| 71 | Y | 4473 | Y | A |
| 11 | Y | 601 | Y | A |
| 314 | N | 19995 | N | B |
| 407 | N | 572 | N | B |
| 531 | N | 2934 | Y | C |
| ... | ... | ... | ... | ... |
| 155 | N | 1972 | N | B |

FIG. 15

METHOD AND SYSTEM FOR COMPRESSING DATA

BACKGROUND OF THE INVENTION

This invention relates generally to imaging systems capable of operation in multiple modalities, and more particularly to an apparatus and method for compressing imaging data generated by a multi-modality imaging system.

Multi-modality imaging systems are capable of scanning using different modalities, such as, for example, Positron Emission Tomography (PET), Single Photon Emission Computed Tomography (SPECT), and Computed Tomography (CT). During operation of a PET imaging system for example, a patient is initially injected with a radiopharmaceutical that emits positrons as it decays. The emitted positrons travel a relatively short distance before they encounter an electron, at which point an annihilation occurs whereby the electron and positron are annihilated and converted into two gamma rays each having an energy of 511 keV. The two gamma rays are directed in nearly opposite directions and detected approximately simultaneously by two separate detector crystals, also commonly referred to as scintillators or scintillator crystals, in the PET scanner.

During a typical scan, the PET imaging system detects and records millions of gamma ray events, referred to herein as racy data. The rate data is typically stored as a list of events in a list file or histogrammed and stored as a histogram file. The list files may include fifteen million events per second resulting in the files being relatively large in size. The rack data is processed by a coincidence processor module to determine and record annihilation events. Typically the coincidence processor module analyzes the racy data to determine if any two of the individual gamma ray events occurred within a small pre-determined time window. If two gamma ray events are detected within a relatively short timeframe, referred to as a coincidence timing window, an event called a prompt is recorded along the line connecting the two crystals, sometimes referred to as a line-of-response (LOR).

The coincidence processor module may determine that of fifteen million gamma ray events detected, five million annihilation events have occurred. While the resulting list file of annihilation events is typically smaller than a file that includes only single gamma ray detected events, the list file of annihilation events is still typically several gigabytes in size. In one case, the list file of annihilation events is transmitted to a histogrammer. For each annihilation event, the histogrammer reads the current count value from a cell of the histogram, modifies the count value by incrementing or decrementing it, and writes the modified value back to the cell.

As imaging system technology advances the quantity of rack data increases. For example, the introduction of higher resolution detectors having more but smaller detector crystals, faster scintillators/detectors to improve sensitivity and count rate capability increased Axial FOVs, etc. As a result, of technological advances, the data word size of a coincidence event has increased and will continue to increase for PET scanners of the future. The previously stated PET Imaging scanner trends toward greater number of detector crystals, and increased Time-Of-Flight (TOF) timing precision and resolution, etc., coupled with the increased reliance on list files, retrospective list replay to produce gated, dynamic and/or static frames of data from a single PET scan are factors that will increase the reliance on list data and therefore increase the cost of streaming and storing list data. As a result, the increased quantity of raw data results in an increased processing demand on the histogrammer as will as an increased demand for additional storage space to store list files having a greater size.

BRIEF DESCRIPTION OF THE INVENTION

In one embodiment a method for compressing imaging data is provided. The method includes acquiring a stream of imaging data, and dividing the stream of imaging data into a plurality of interstices, each interstice including a plurality of detected events. The method also includes classifying the detected events within each interstice based on a probability of occurrence of the detected event, and re-ordering the detected events within each interstice based on the probability of occurrence to compress the image data. The method further includes re-ordering the detected events based on at least one a ring pair identification number and a derived transaxial angle.

In another embodiment, a medical imaging system including a computer is provided. The computer is programmed to acquire a stream of imaging data and divide the stream of imaging data into a plurality of interstices, each interstice including a plurality of detected events. The computer is also programmed to classify the detected events within each interstice based on a probability of occurrence of the detected event, and re-order the detected events within each interstice based on the probability of occurrence to compress the image data.

In a further embodiment, a computer readable medium is provided. The computer readable medium is programmed to instruct a computer to acquire a stream of imaging data, and divide the stream of imaging data into a plurality of interstices, each interstice including a plurality of detected events. The computer readable medium is also programmed to instruct a computer to classify the detected events within each interstice based on a probability of occurrence of the detected event, and re-order the detected events within each interstice based on the probability of occurrence to compress the image data.

BRIEF DESCRIPTION OF THE DRAWINGS

FIG. 8 is an exemplary table that is used with the method shown in FIG. 7.

FIG. 15 is an exemplary table that is generated using the method shown in FIG. 7.

DETAILED DESCRIPTION OF THE INVENTION

Figure 1:
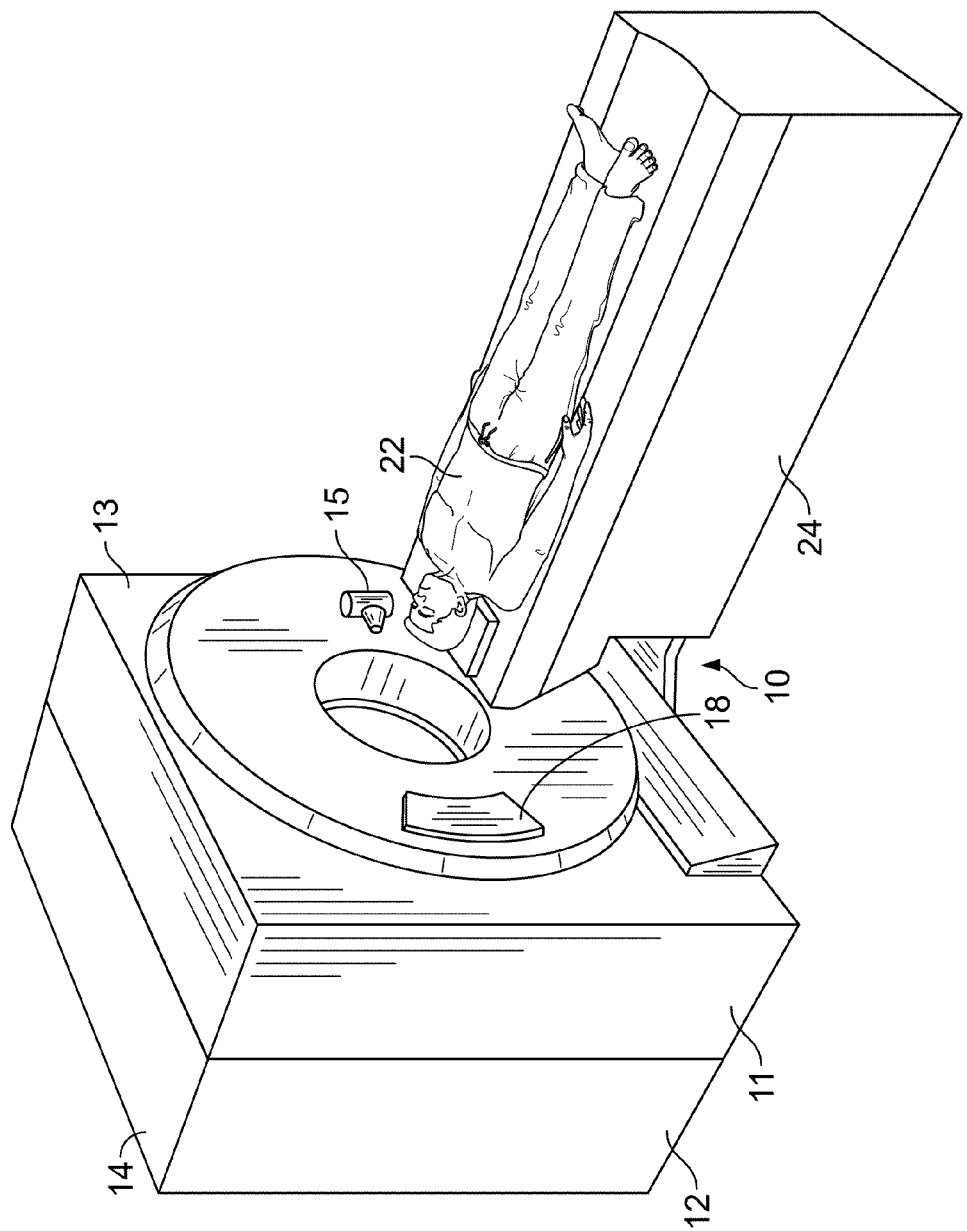
FIG. 1 is a pictorial view of an exemplary multi-modality imaging system in accordance with an embodiment of the present invention.

The foregoing summary as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate, or are configured to generate, at least one viewable image.

Figure 2:
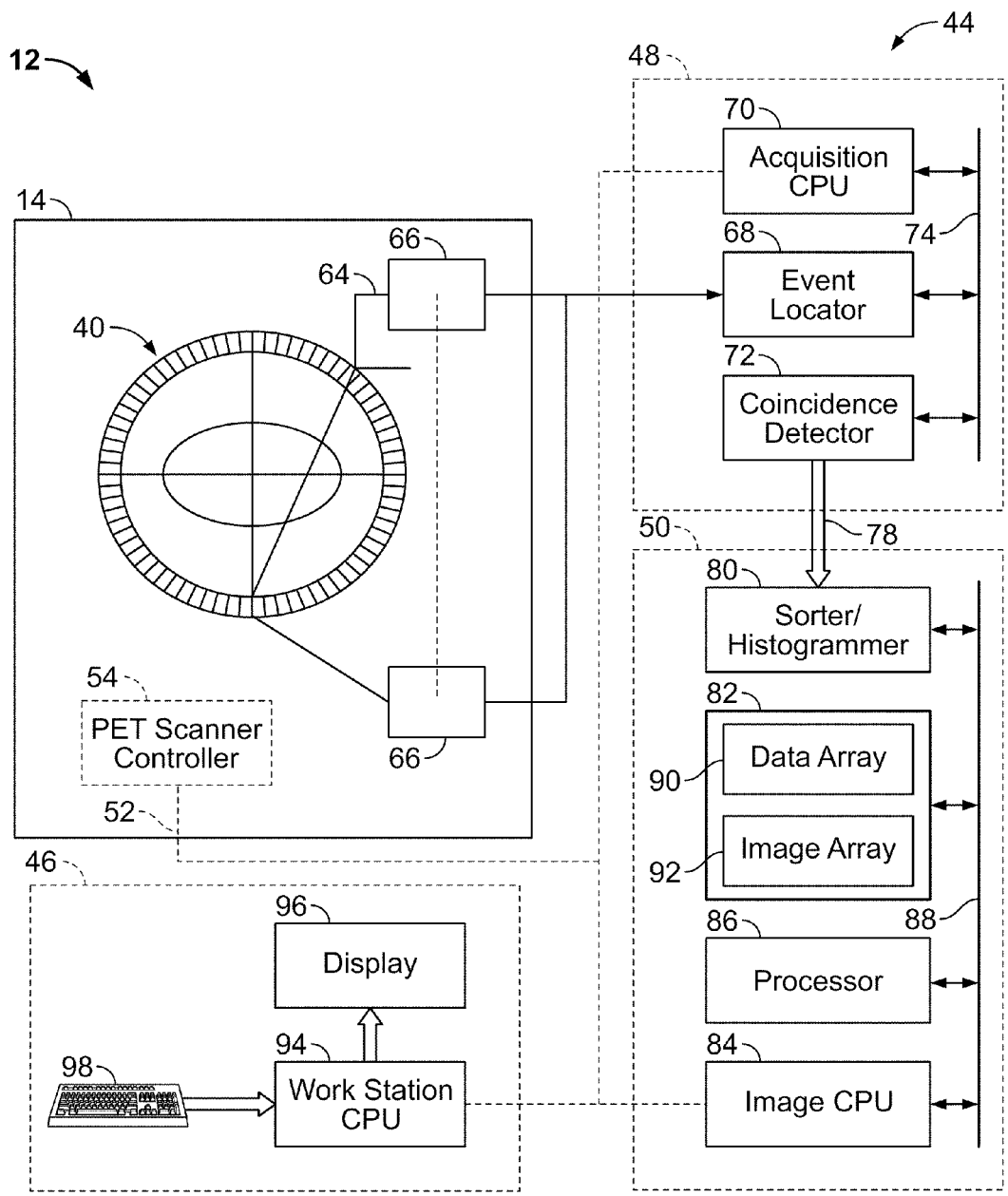
FIG. 2 is a block schematic diagram of the system illustrated in FIG. 1 in accordance with an embodiment of the present invention.

Various embodiments of the invention provide a multi-modality imaging system 10 as shown in FIGS. 1 and 2. Multi-modality imaging system 10 may be any type imaging system for example, different types of medical imaging systems, such as a Positron Emission Tomography (PET), a Single Photon Emission Computed Tomography (SPECT), a Computed Tomography (CT), an ultrasound system Magnetic Resonance Imaging (MRI) or any other system capable or generating tomographic images. The various embodiments are not limited to multi-modality medical imaging systems, but may be used on a single modality medical imaging system such as a stand-along PET imaging system or a stand-along SPECT imaging system for example. Moreover, the various embodiments are not limited to medical imaging systems for imaging human subjects, but may include veterinary or non-medical systems for imaging non-human objects etc.

Referring to FIG. 1, the multi-modality imaging system 10 includes a first modality unit 11 and a second modality unit 12. The two modality units enable the multi-modality imaging system 10 to scan an object or patient in a first modality using the first modality unit 11 and to scan the object or patient in a second modality using the second modality unit 12. The multi-modality imaging system 10 allows for multiple scans in different modalities to facilitate an increased diagnostic capability over single modality systems. In one embodiment, multi-modality imaging system 10 is a Computed Tomography/Positron Emission Tomography (CT/PET) imaging system 10, e.g. the first modality 11 is a CT imaging system 11 and the second modality 12 is a PET imaging system 12. The CT/PET system 10 is shown as including a gantry 13 representative of a CT imaging system and a gantry 14 that is associated with a PET imaging system. As discussed above, modalities other than CT and PET may be employed with the multi-modality imaging system 10.

The gantry 13 includes an x-ray source 15 that projects a beam of x-rays toward a detector array 18 on the opposite side of the gantry 13. Detector array 18 is formed by a plurality of detector rows (not shown) including a plurality of detector elements which together sense the projected x-rays that pass through a medical patient 22. Each detector element produces an electrical signal that represents the intensity of an impinging x-ray beam and hence allows estimation of the attenuation of the beam as it passes through the patient 22. During a scan to acquire x-ray projection data, gantry 13 and the components mounted thereon rotate about a center of rotation.

FIG. 2 is a block schematic diagram of the PET imaging system 12 illustrated in FIG. 1 in accordance with an embodiment of the present invention. The PET imaging system 12 includes a detector ring assembly 40 including a plurality of detector crystals. The PET imaging system 12 also includes a controller or processor 44, to control normalization and image reconstruction processes. Controller 44 is coupled to an operator workstation 46. Controller 44 includes a data acquisition processor 48 and an image reconstruction processor 50, which are interconnected via a communication link 52. PET imaging system 12 acquires scan data and transmits the data to data acquisition processor 48. The scanning operation is controlled from the operator workstation 46. The data acquired by the data acquisition processor 48 is reconstructed using the image reconstruction processor 50.

The detector ring assembly 40 includes a central opening in which an object or patient, such as patient 22 may be positioned, using, for example, a motorized table 24 (shown in FIG. 1). The motorized table 24 is aligned with the central axis of detector ring assembly 40. This motorized table 24 moves the patient 22 into the central opening of detector ring assembly 40 in response to one or more commands received from the operator workstation 46. A PET scanner controller 54, also referred to as the PET gantry controller, is provided (e.g., mounted) within PET system 12. The PET scanner controller 54 responds to the commands received from the operator workstation 46 through the communication link 52. Therefore, the scanning operation is controlled from the operator workstation 46 through PET scanner controller 54.

Figure 3:
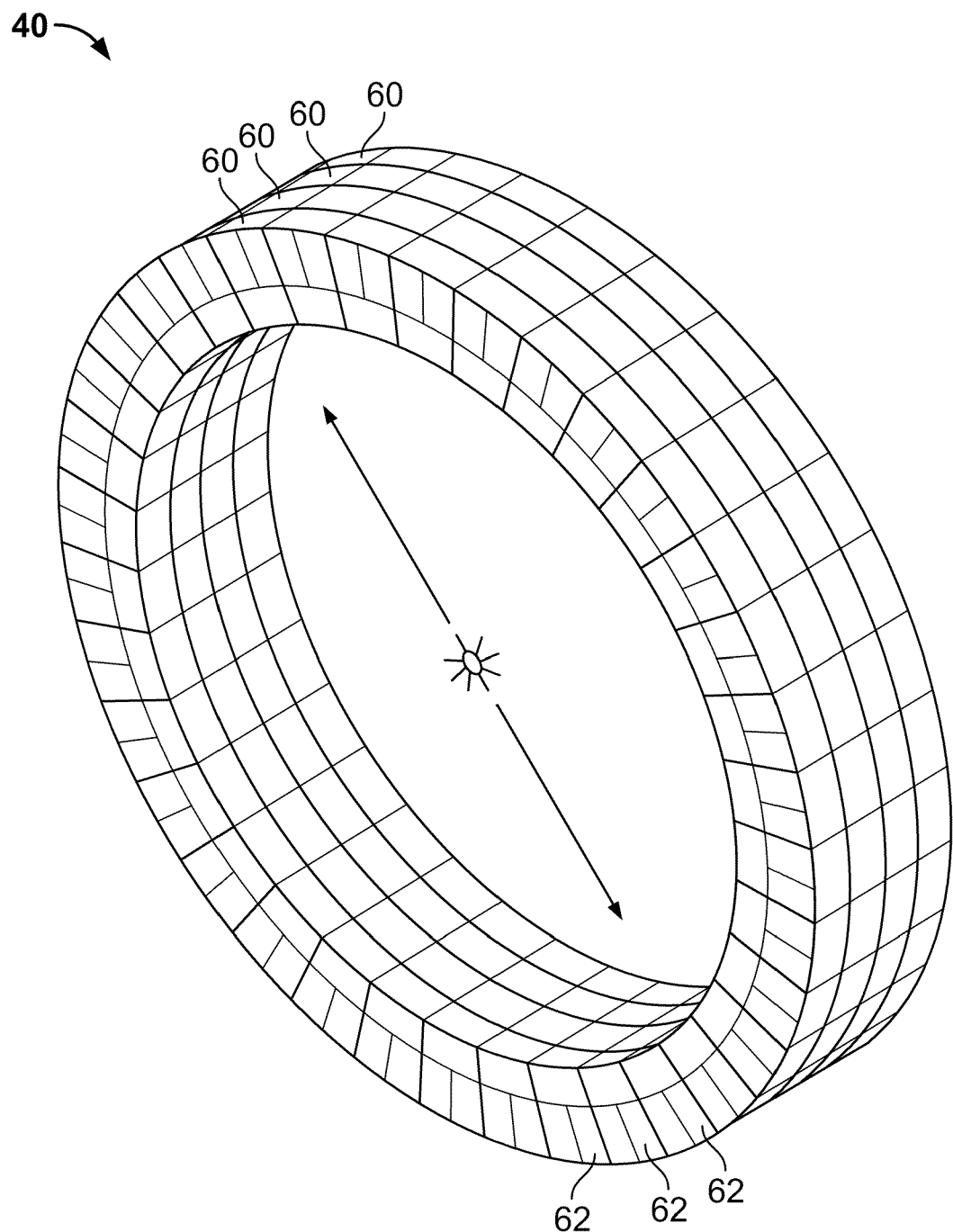
FIG. 3 is a perspective view of the exemplary detector ring assembly shown in FIG. 2 in accordance with an embodiment of the present invention.

FIG. 3 is a perspective view of the exemplary detector ring assembly 40 (shown in FIG. 2). The detector ring assembly 40 includes a plurality of detector rings 60. IN the exemplary embodiment detector ring assembly 40 includes twenty-four individual detector rings 60. It should be realized that the quantity of detector rings 60 is exemplary only and that the methods described herein may be applied to any exemplary detector ring assembly having N individual detector rings 60, wherein N≧2. Each detector ring 60 also includes N scintillator crystals 62. It should be realized that the quantity of scintillator crystals 62 is exemplary only and that the methods described herein may be applied to any exemplary detector ring 60 having N individual scintillator crystals 62, wherein N≧2. In the exemplary embodiment, each detector ring 60 includes 568 individual scintillator crystals 62.

Referring again to FIG. 2, during operation, when a photon collides with a crystal 62 on a detector ring 60, it produces a scintilla on the crystal. Each photomultiplier tube produces an analog signal that is transmitted on communication line 64 (shown in FIG. 2) when a scintillation event occurs. A set of acquisition circuits 66 is provided to receive these analog signals. Acquisition circuits 66 produce digital signals indicating the 3-dimensional (3D) location and total energy of the event. The acquisition circuits 66 also produce an event detection pulse, which indicates the time or moment the scintillation event occurred. These digital signals are transmitted through a communication link, for example, a cable, to an event locator circuit 68 in the data acquisition processor 48.

The data acquisition processor 48 includes the event locator circuit 68, an acquisition CPU 70 and a coincidence detector 72. The data acquisition processor 48 periodically samples the signals produced by the acquisition circuits 66. The acquisition CPU 70 controls communications on a back-plane bus 74 and on the communication link 52. The event locator circuit 68 processes the information regarding each valid event and provides a set of digital numbers or values indicative of the detected event. For example, this information indicates when the event took place and the position of the scintillation crystal 62 that detected the event. An event data packet is communicated to the coincidence detector 72 through the back-plane bus 74. The coincidence detector 72 receives the event data packets from the event locator circuit 68 and determines if any two of the detected events are in coincidence. Coincidence is determined by a number of factors. First, the time markers in each event data packet must be within a predetermined time period, for example, 12.5 nanoseconds, of each other. Second, the LOR formed by a straight line joining the two detectors that detect the coincidence event should pass through the field of view in the PET imaging system 12. Events that cannot be paired are discarded. Coincident event pairs are located and recorded as a coincidence data packet that is communicated through a physical communication link 78 to a sorter/histogrammer 80 in the image reconstruction processor 50.

The image reconstruction processor 50 includes the sorter/histogrammer 80. During operation, sorter/histogrammer 80 generates a data structure known as a histogram. A histogram includes a large number of cells, where each cell corresponds to a unique pair of detector crystals in the PET scanner. Because a PET scanner typically includes thousands of detector crystals, the histogram typically includes millions of cells. Each cell of the histogram also stores a count value representing the number of coincidence events detected by the pair of detector crystals for that cell during the scan. At the end of the scan, the data in the histogram is used to reconstruct an image of the patient. The completed histogram containing all the data from the scan is commonly referred to as a "result histogram." The term "histogrammer" generally refers to the components of the scanner, e.g., processor and memory which carry out the function of creating the histogram.

The image reconstruction processor 50 also includes a memory module 82, an image CPU 84, an array processor 86 and a communication bus 88. During operation, the sorter/histogrammer 80 counts all events occurring along each projection ray and organizes the events into 3D data. This 3D data, or sinograms, is organized in one exemplary embodiment as a data array 90. Data array 90 is stored in the memory module 82. The communication bus 88 is linked to the communication link 52 through the image CPU 84. The image CPU 84 controls communication through communication bus 88. The array processor 86 is also connected to the communication bus 88. The array processor 86 receives data array 90 as an input and reconstructs images in the form of image arrays 92. Resulting image arrays 92 are then stored in memory module 82.

The images stored in the image array 92 are communicated by the image CPU 84 to the operator workstation 46. The operator workstation 46 includes a CPU 94, a display 96 and an input device 98. The CPU 94 connects to communication link 52 and receives inputs, e.g., user commands, from the input device 98. The input device 98 may be, for example, a keyboard, mouse, a touch-screen panel, and/or a voice recognition system etc. Through input device 98 and associated control panel switches, the operator can control the operation of the PET imaging system 12 and the positioning of the patient 22 for a scan. Similarly the operator can control the display of the resulting image on the display 96 and can perform image-enhancement functions using programs executed by the workstation CPU 94.

Figure 4:
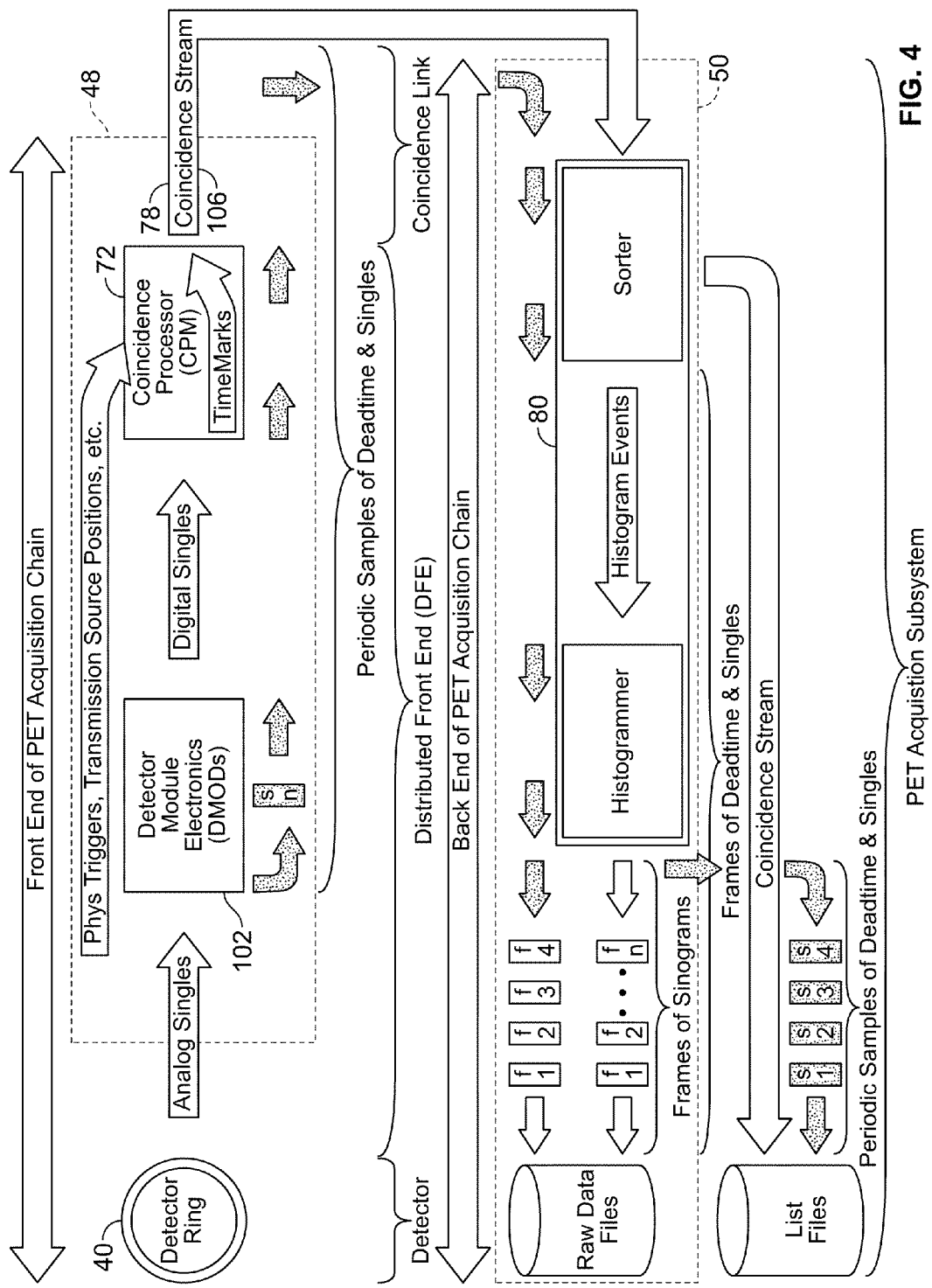
FIG. 4 is a simplified block diagram of an exemplary data acquisition process performed by the PET imaging system shown in FIG. 2 in accordance with an embodiment of the present invention.

FIG. 4 is a simplified block diagram of an exemplary data acquisition process performed by the PET imaging system 12 shown in FIG. 2 in accordance with an embodiment of the present invention. As discussed above, gamma rays resulting from positron emissions in the detector field of view are recorded by the detector assembly 40 where the analog signals are digitized and energy filtered by what is typically referred to as a set of detector module electronics (DMODs). Although FIG. 4 illustrates a single DMOD 102, it should be realized that the PET imaging system 12 may include a plurality of DMODs 102 that are incorporated into the detector assembly 40. During operation, the digitized signals generated by the detector ring assembly 40, referred to herein as "singles", are transmitted from the DMODs 102 to the coincidence detector 72, also referred to herein as the Coincidence Processor Module (CPM) 72. The CPM 72 receives the digitized singles from the DMOD 102 and pairs up the singles events. Specifically the CPM 72 determines if two gamma ray events are detected within a relatively short timeframe, referred to as the coincidence timing window, and if so, pairs the two gamma rays together in a group referred to herein as a coincidence event.

Figure 5:
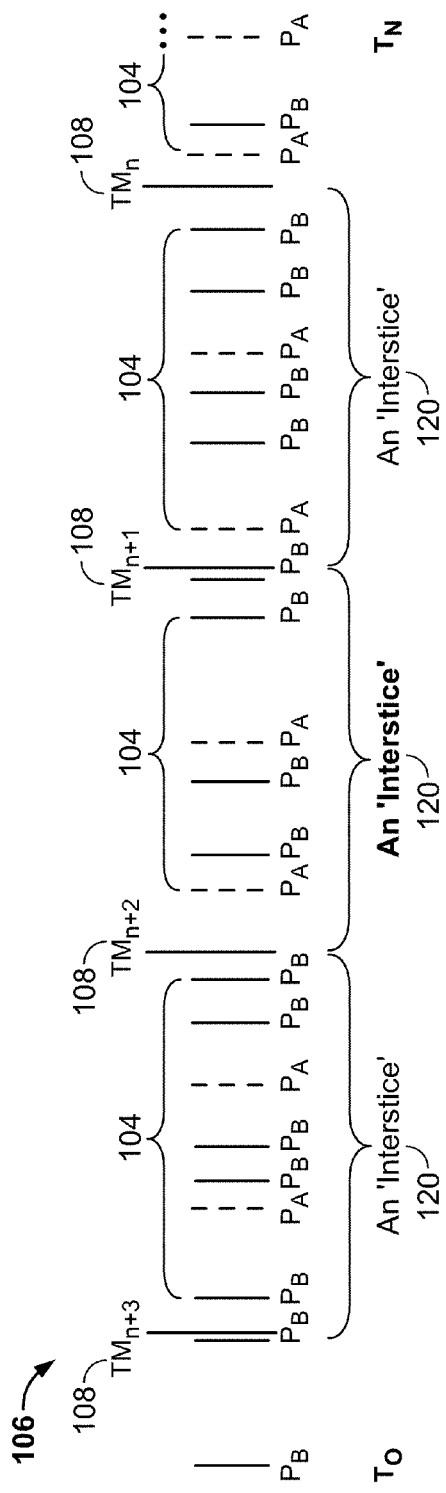
FIG. 5 is a portion of an exemplary coincidence stream that may be generated by PET imaging system shown in FIG. 2 in accordance with an embodiment of the present invention.

FIG. 5 is a portion of an exemplary coincidence stream 106 that may be generated by CPM 72 during operation. As shown in FIG. 5, in the exemplary embodiment, the detected events 104 or prompts 104 are merged chronologically from a time $T_0$ to a time $T_N$ to form a coincidence stream 106. The CPM 72 also inserts time markers 108 ($TM_{n+3} \ldots TM_n$) into the coincidence stream 106. In operation, the time markers 108 divide the coincidence stream 106 into approximately equal subdivision of data. Specifically the time markers 108 are generated by the CPM 72 at a fixed frequency and merged into the stream of coincidence events 104 to enable the coincidence events 104 to be sorted at the backend of the acquisition chain into frames of events based on relative time. In the exemplary embodiment, the time markers 108, or timestamps, may be inserted into the coincidence stream 104 at an arbitrary frequency or a frequency that is driven by the scanner's imaging applications. For example, to perform relatively high precision framing for cardiac or respiratory gating, the period between time markers 108 is on the order of a few milliseconds. It should be realized that the time markers 108 may be inserted into the coincidence stream at any frequency based on the acquisition parameters of the image reconstruction process desired. Therefore, inserting the time stamps 108 ever few milliseconds as discussed above is only one example of the frequency in which the time stamps 108 may be inserted.

Figure 6:
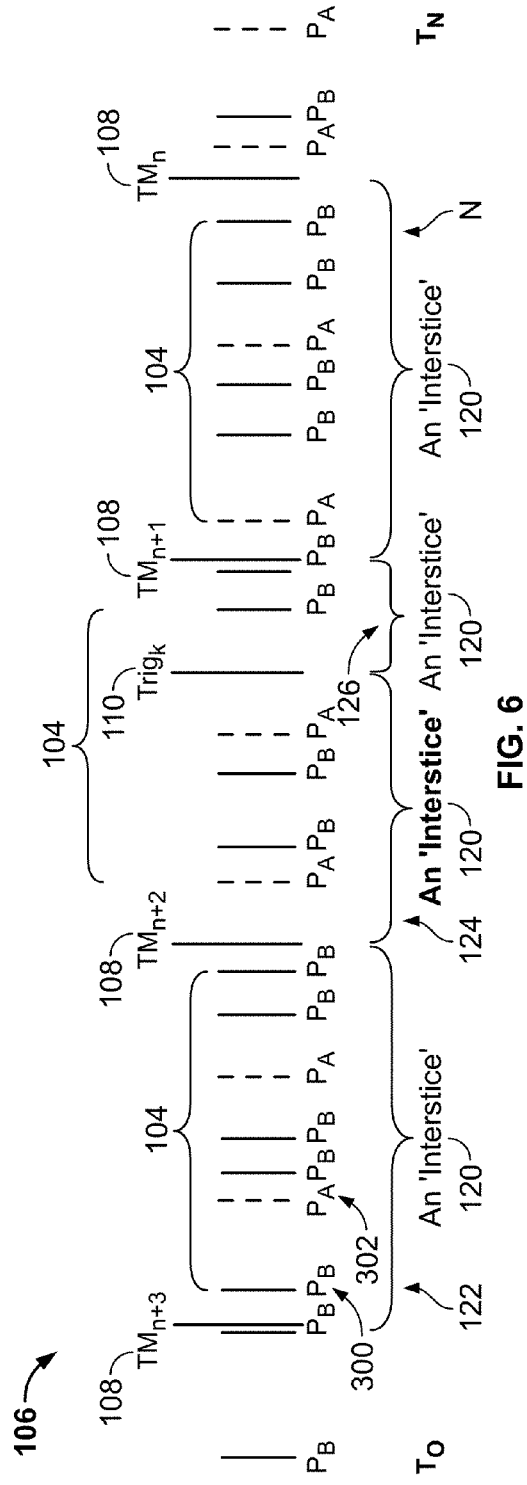
FIG. 6 is another exemplary portion of the coincidence stream shown in FIG. 5 that may be generated by PET imaging system shown in FIG. 2 in accordance with an embodiment of the present invention.

FIG. 6 is another exemplary portion of the coincidence stream 106 that also includes at least one, and more typically, a plurality of physiological trigger events 110. The physiological trigger events 110 are received from an externally connected cardiac or respiratory monitor, for example, and are then asynchronously and chronologically merged into the coincidence stream 106 at and by the CPM 72. The physiological trigger events 110 represent a start of a cardiac or respiratory cycle and are used in conjunction with the time markers 108 to frame the coincidence events 104 based on either cardiac or respiratory physiological cycle or phase. As such, the physiological triggers 110 may be generated using a physiological sensor, such as for example, a respiratory signal or trace, or a cardiac signal. As used herein, a prompt refers to any of the coincidence pairs that have been determined to be coincidence events 104 by the CPM 72. As such, as discussed below, the coincidence stream 106 includes a plurality prompts.

Referring again to FIG. 4, the coincidence stream 106 is then transmitted to the sorter/histogrammer 80 via the physical link 78, also referred to as the coincidence link 78 shown in FIG. 2. The sorter/histogrammer 80 is often referred to as the backend of the acquisition chain. The sorter/histogrammer 80 receives the coincidence stream 106 and converts the coincident events 104 from detector space coordinates to sinogram coordinates. The sorter/histogrammer 80 histograms the events to produce a set of sinograms that is used as an input to the image reconstruction process. The sinograms are generated as frames based on time, and optionally physiological cardiac or respiratory phase. In addition to generating sinograms, the sorter/histogrammer 80 is also programmed to save the coincidence stream 106 to a file system for subsequent replay. This capturing of the entire coincidence stream 106, including time markers 108 and physiological trigger events 110, in its original chronological order as generated by the CPM and is often referred to as a List Mode record. The files produced are referred to as List Files. During a replay operation, the List Files are fetched from the online repository of List Files and played back into the Sorter/Histogrammer 80 to produce new types of framed Sinograms.

As discussed briefly above, the size of the exemplary coincidence stream 106 may exceed five gigabytes necessitating a need for additional storage space and/or increased processing requirements. Moreover, current trends in PET imaging technology may further increase the size of the exemplary coincidence stream 106.

Figure 7:
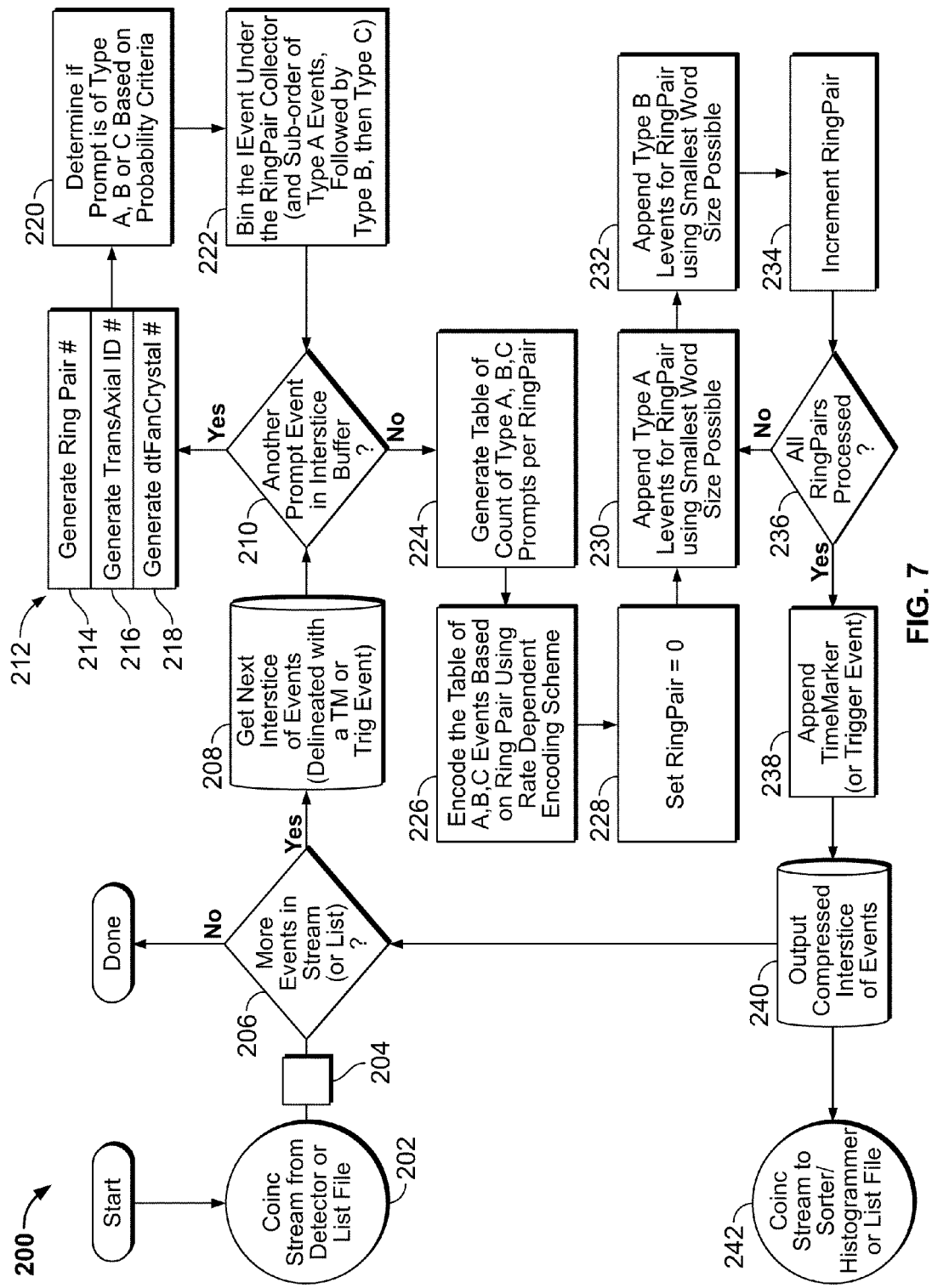
FIG. 7 is a flowchart illustrating an exemplary method for compressing imaging data.

Accordingly, FIG. 7 is a flowchart illustrating an exemplary method 200 for compressing a stream of data, such as the exemplary PET coincidence event list or stream 106 shown in FIGS. 5 and 6. As used herein, the term "stream of data" may refer to either the coincidence stream of data 106 generated during the scanning process, or to a list file that includes the coincidence stream of data 106. In the exemplary embodiment method 200 includes acquiring 202 a stream of data 106. Acquiring 202 may include acquiring the stream of data during the scanning process using the CPM 72 for example, or acquiring a stored stream of data, such as a list file from a memory or storage device. Method 200 further includes dividing 204 the stream of data 106 into a plurality of interstices 120 as shown in FIGS. 5 and 6. In the exemplary embodiment, each interstice 120 includes a plurality of prompts 104.

In one embodiment, the interstices 120 may be generated using the time markers 108. More specifically the plurality of prompts 104 occurring between a pair of chronologically sequential time markers 108 form a single interstice 120. For example, assuming that the stream of data 106 or list file being compressed includes approximately 200 million coincidence events that are separated by approximately 180,000 time markers 108, a separate interstice 120 would be generated for each set of prompts occurring between each pair of chronological time marker 108, e.g. approximately 180,000 interstices 120 are generated for the exemplary stream of data 106. Optionally dividing the stream of data 204 may include dividing the stream of data 106 using the physiological triggers 110. In another option, dividing the stream of data 106 may include dividing the stream of data using both the time markers 108 and the physiological triggers 110. In the exemplary embodiment, the interstices are acquired in a chronological order. For example, referring again to FIG. 6, the first interstice 122 is acquired and processed as discussed herein. The next subsequent interstice in chronological order, e.g. interstice 122 is then processed followed by interstices 124, until the last or the Nth interstice is processed. The method 200 is performed on each interstice 120 in the stream of data 106.

Method 200 further includes determining 206 if any of the N interstices 120 remain to be processed. If no, method 200 is complete. If yes, method 200 proceeds to the next processing step. More specifically method 200 further includes acquiring 208 the next subsequent interstice 120, such as interstice 122 shown in FIG. 6. For each interstice 120, the method 200 further includes acquiring 210 a prompt, such as prompt 300 of interstice 122 shown in FIG. 6. The prompt 300 is then processed to generate an IEvent in step 212.

In step 212 the prompt 300 is remapped to generate the IEvent that reduces or compresses the size of the data used to identify the prompt. The remapped prompts are referred to herein as IEvents or intermediate events, indicating that the size or bits used to identify the prompt originally have been reduced or compressed to generate an IEvent for each prompt 104. As discussed above, when each prompt 104 is generated, the prompt 104 includes information that identifies both a pair of axial coordinates and a pair of transaxial coordinates of the crystals that are used to generate the prompt. More specifically each prompt or coincidence event is recorded along the line connecting the two crystals, sometimes referred to as a line-of-response (LOR). In one embodiment imaging system 10 identifies each crystal using a pair of coordinates that exactly identify the location of each crystal, in the pair of crystals forming the coincidence event, in the detector 40. Optionally imaging system 10 may utilize various detector crystal coordinates schemes to identify the location of each crystal. For example, imaging system 10 may include arbitrary X-axis, Y-axis and Z-axis, or module, block and X, Y crystals within a block as examples. In the exemplary embodiment, the detector 40 is used to describe the compression scheme discussed herein that uses a crystal coordinate system of (axial transaxial) coordinates to identify a specific crystal within the set of detector crystals. The compression scheme however is not limited to (axial, transaxial) detector coordinate systems.

During operation, each crystal is identified using both an axial component (XtalAxialID) and a transaxial component (XtalTransAxialID) As used herein, the axial component represents the ring in which the crystal lies in the axial direction, and the transaxial component represents the crystal in the identified ring in the transaxial or radial direction of the specified ring. Assuming that exemplary detector includes twenty-four rings or crystals disposed in the axial direction and each ring includes 600 crystals, each crystal in the coincidence event is identified using two separate numbers, the first number representing the axial ring ranging from 1-24 and the second number representing the transaxial location in the specified ring ranging from 1-600. As a result, conventional imaging systems generate four separate numbers for each coincidence event to reconstruct images, wherein each number requires X bits to store the data. As will be clearly understood, the exemplary data stream 106 may include millions of prompts 104, wherein each prompts 104 in the conventional imaging system is identified using four distinct number, two crystal axial ID numbers and two crystal transaxial ID numbers. It should be realized that the numbers used to identify the axial and transaxial location of each crystal is exemplary only and that the ranges of these numbers vary depending on the geometry of the detector being used. For example, in the exemplary embodiment described herein, the detector 40 includes 24 rings wherein each ring includes 600 crystals. However, other detectors having more or less rings and more or less crystals per ring may be used.

To reduce or compress the size of the exemplary coincidence stream 106, at step 212 the prompt 300 is remapped. The step 212 will be discussed using Table 1 below. In the exemplary embodiment, the resulting IEvent data, after remapping the original prompt in the stream of data 106 includes the RingPairID number, the TraxID number, and the dtFanPairID number.

TABLE 1

| Crystal 1 | Xtal1AxialID (3) | X bits | RingPairID | Y bits |
|---|---|---|---|---|
| Crystal 2 | Xtal1AxialID (18) | X bits | | |
| Crystal 1 | Xtal1TransAxial ID (360) | 10 bits | fanCrystalID | 9 bits |
| Crystal 2 | Xtal2TransAxial ID (240) | 10 bits | TraxID | 9 bits |
| | ΔTime (Time of Flight) | 10 bits | ΔT | 7 bits |
| | ΔT/fanCrystalID | 16 bits | dtFanPairID | 15 bits |

For example, in the exemplary embodiment, the two crystals identified as forming the coincidence event 300 will be referred to herein as Crystal 1 and Crystal 2, wherein the location of Crystal 1 is identified as (3, 340), e.g. the 3rd axial ring and the 340th crystal in the $3^{rd}$ axial ring, and Crystal 2 is identified as (18, 240) e.g. the 18th axial ring and the 240th crystal in the 18th axial ring. To reduce the size of the exemplary coincidence stream 106, remapping 212 includes generating 214 a single number referred to herein as the RingPairID number. More specifically the axial ID's of each of crystals 1 and 2 (e.g. 3 and 18) are remapped to form a single RingPairID number that includes less bits than the combination of bits used to identify both Crystal 1 and 2 Axial ID's. For example, referring to FIG. 8, and assuming that the AxialID of Crystal 1 is 3 and the AxialID of Crystal 2 is 18, using Table 2 shown in FIG. 8, the Axial ID's of Crystals 1 and 2 are remapped to a single number, e.g. the RingPairID number=65. The RingPairID number includes Y bits wherein Y<X. It should be realized that coincidence stream 106 generally includes millions of prompts 104 and that the axial ID's for each prompt 104 are remapped to generate a RingPairID number that is associated with the particular prompt being remapped, and thus substantially reduces or compresses the size of the coincidence stream 106.

In the exemplary embodiment the method or compression scheme described herein performs data reduction by either re-ordering the prompts in an interstice based on an attribute of the prompts that typically has small variance faith respect to the probability of the prompt occurrence, and/or using less bits to encode the more likely occurring prompts. These principles will be elaborated in subsequent paragraphs.

In the exemplary embodiment, when re-ordering the prompts within an interstice for the exemplary detector and prompt event content, the 'ring pair' attribute is utilized for identifying the most likely occurring prompts. Optionally the 'transaxial angle' attribute may be utilized for identifying the most likely occurring prompts.

Figure 10:
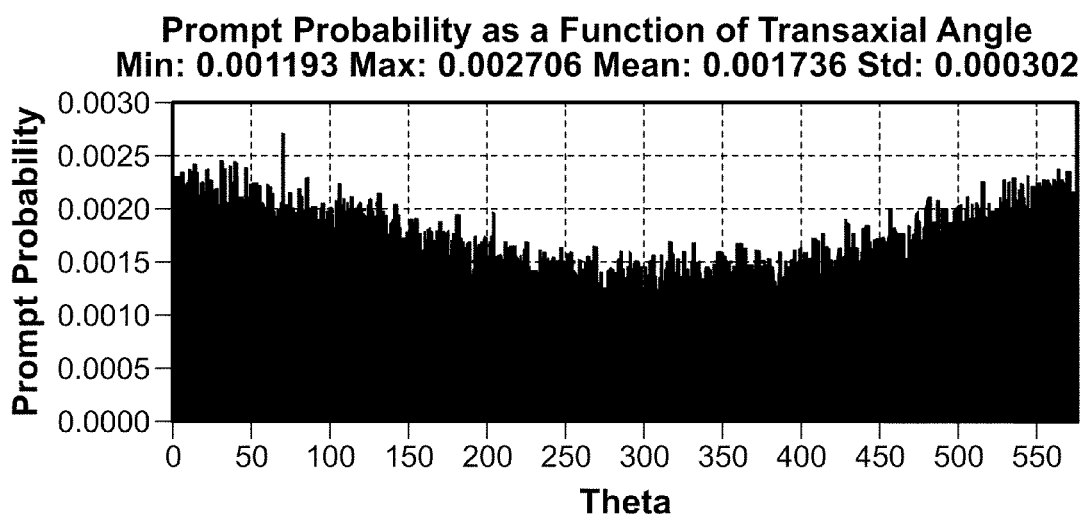
FIG. 10 is a histogram illustrating an exemplary distribution of prompts.
Figure 11:
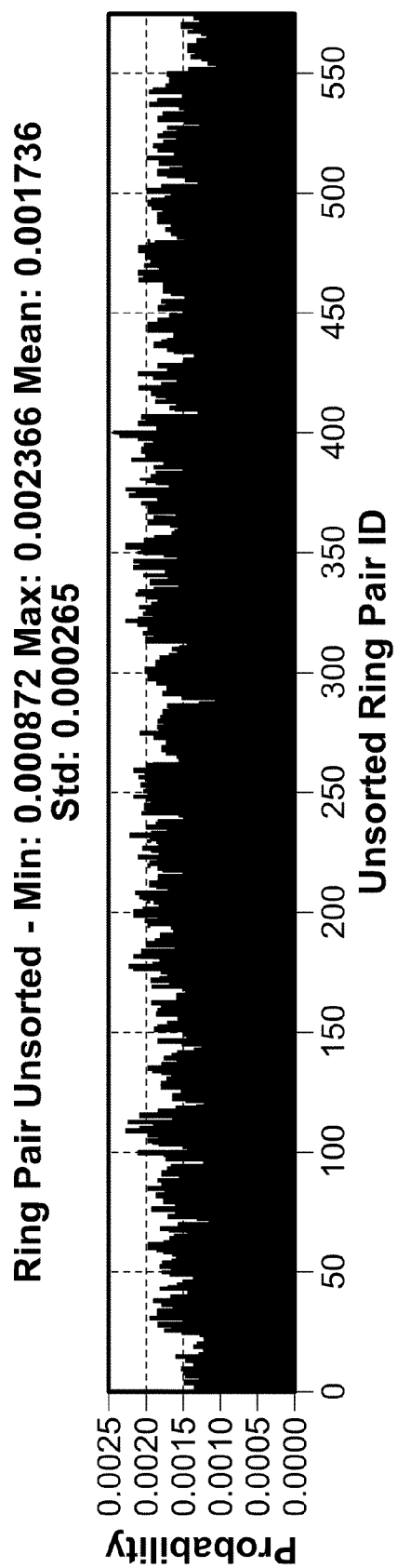
FIG. 11 is a graphical illustration of the uniformity of prompt probability as a function of the ring pairs.

More specifically to elaborate on the optional choice of selecting a good attribute of the prompt definition for first order event re-ordering, it should be noted that during operation of the exemplary detector 40, the variance of counts as a function of transaxial angle is relatively low, and furthermore, the variance between consecutive angles is low. This is also true for 'ring pairs'. So both are good attributes for the first order re-order of prompts within an interstice. For example, the transaxial angle, θ, that describes the LOR of the prompt can be derived from the transaxial information in the Prompt by performing a 1:1 correspondence using the sum of the high and low crystal-pair IDs. The resulting prompt probability as a function of theta for the exemplary scanner list data is reflected in FIG. 10. In the exemplary embodiment the Theta Prompt distribution is approximately equivalent to the Ring Pair uniformity with respect to mean and standard deviation, reflected in FIG. 11. As such, the Theta Angle can also be used to minimize the encoded high-crystal transaxial information. Prompts between time markers (or physiological triggers) can be reordered by the derived theta angle or ring pair, and information can be recorded in the compressed data to indicate hows many events and where within the compressed data the events for a given theta angle or ring pair would be found. The choice of "ring pair" or "transaxial angle" illustrates various embodiments of the compression scheme.

In a preferred embodiment of the compression scheme, transaxial information other than the derived transaxial angle associated with the prompt's LOR, can be used to identify the most likely occurring prompts. For example, Xtal2TransAxial ID can arbitrarily be renumbered with respect to minimum ID value to maximum ID value, specifically reversing the assignment of IDs from maximum to minimum ID values. Using the exemplary ID's for prompt 300 presented above, Xtal2TransAxID=240. The quantity of crystals in the detector 40 is 600. As such, traxID[240]=Xtal2TransAxID[600−240]=360.

To reduce the size of the exemplary coincidence stream 106, remapping 212 includes generating 216 a single number referred to herein as the TraxID number. As discussed above, each crystal is identified using both an axial component (Xtal1AxialID) and a transaxial component (XtalTransAxialID). As used herein, transaxial component represents the location of the crystal in the transaxial or radial direction in the specified ring. In the exemplary embodiment the Xtal2TransAxial ID is renumbered using the following exemplary reverse assignment algorithm:

traxID[i]=Xtal2TransAxID[600]−i

Figure 9:
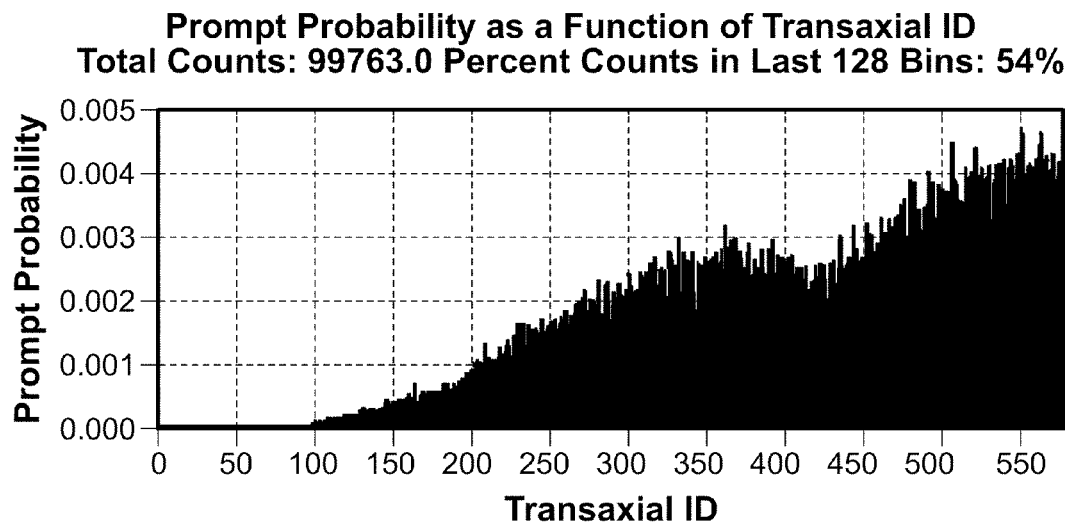
FIG. 9 is a histogram illustrating an exemplar distribution of prompts.

The previously described derived transaxial angle, often referred to as theta, θ, does not intrinsically reflect a one-to-one mapping to the "high" transaxial ID of the detector pair since in one embodiment the CPM 72 performs a swap of the transaxial IDs of the crystal pair such that the hiXtalTransAxialID is always greater than the loXtalTransAxialID. In use, the reverse assignment algorithm simplifies the sorter 80 conversion from detector space to Sinogram space and aids the preferred embodiment of the compression scheme. Since in this preferred embodiment, the Sinogram radial component is derived from the difference of the crystal pair and sorter, per-event testing for negative difference is avoided if hiXtalTransAxID is always greater than loXtalTransAxID. Consequently the distribution of Prompts as a function of hiXtalTranAxID is not uniform, as shown in FIG. 9. Moreover, the non-uniformity associated with the hiXtalTranAxID can be leveraged for identifying the more probable occurring prompts, and, a maximum of nine bits are now used to encode the valid ID's of the hiXtalTranAxID. Also note that some hiXtalTransAxID crystals are never valid due to the swapping of the high and low crystals in the crystal pair of the Prompt.

Optionally, the prompts' crystal pair transaxial information can be described using fewer bits of information by remapping the information as a Function of Transaxial ID and Fan Angle, as opposed to high and low transaxial IDs. Since some Transaxial IDs are rendered invalid by the Scan Field Of View (SFOV) filter applied by the Coincidence Processor. Leveraging the SFOV filter is another variation of embodiment of the compression scheme. In the exemplary embodiment, the detector field of view (DFOV) is approximately 80-90 cm, but the primary area of interest, i.e. the scan field of view (SFOV) is typically 65-70 cm and is often constrained by the physical bore size of the PET or PET/CT scanner. Since most patients can be accommodated by a 70 cm SFOV, in the exemplary embodiment, the prompts that lie outside of the SFOV are filtered, or not generated by the detector front-end electronics, i.e. the Coincidence Processor Module (CPM).

To reduce the size of the exemplary coincidence stream 106, remapping 212 also includes generating 218 a single number referred to herein as the dtFanPairID number. In the exemplary embodiment the dtFanPairID number is a combination of two separate values used to identify the transaxial and time-of-flight information of the in-coincidence crystal pair, e.g. the deltaT number and the fanCrystalID. For example, the dt, or deltaT, value represents the time-of-flight (TOF) information assigned to the exemplary prompt 300. The TOF is the time taken by an annihilation photon to travel from the origin of annihilation to detector elements along the line of response (LOR). The TOF generally cannot be measured directly since the time at which the emission takes place is not known, thus the TOF usually refers to the difference, or deltaT, in the time at which the photons are detected by the detector elements.

Figure 12:
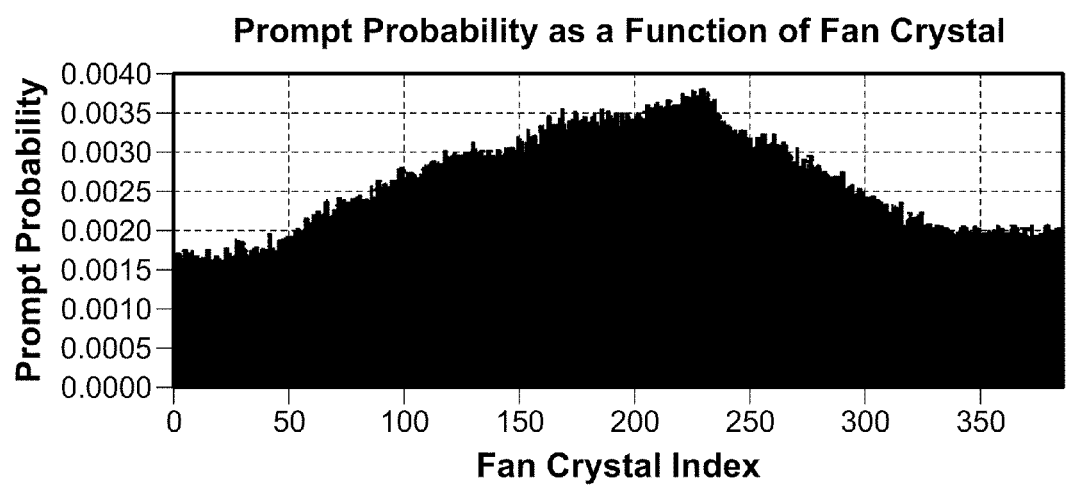
FIG. 12 is a histogram illustrating an exemplary prompt probability per crystal in the fan.

The fanCrystalID number is the assigned index of a given crystal within a fan of a given high transaxial crystal. Assuming that in the exemplary embodiment, the scan field of view is 70 cm, as a general rule, the crystals in the center of the fan are more apt to be busy relative to the outer fan crystals since most patients are typically centered in the FOV, are not 70 cm wide nor cylindrical in shape. As a result, lower numbered fanCrystalIDs are assigned to the crystals associated with the center of the fan. For example, FIG. 12 illustrates a histogram of Prompt probability per crystal in the fan, ignoring all other subfields of the events, for the exemplary imaging system 10 data set. The center of the histogram's longitudinal axis represents the center fan crystal, and the right-most and left-most crystals in the fan equate to the boundaries of the graph's longitudinal axis. In the exemplary embodiment, 48% of the total prompts are contained in the center 8192 cells of the histogram. During operation, each patient exhibits a different distribution based on patient Width and sources of metabolism but as a generalization, the distribution will have characteristics of a bell-shaped curve. It should be recognized that the event TOF (deltaT) sub-parameter has greater variance as a function of the fanCrystalID. This relationship will be made more obvious by looking at the individual deltaT event distribution, followed by the relational deltaT, fanCrystal event distribution as discussed below.

Figure 13:
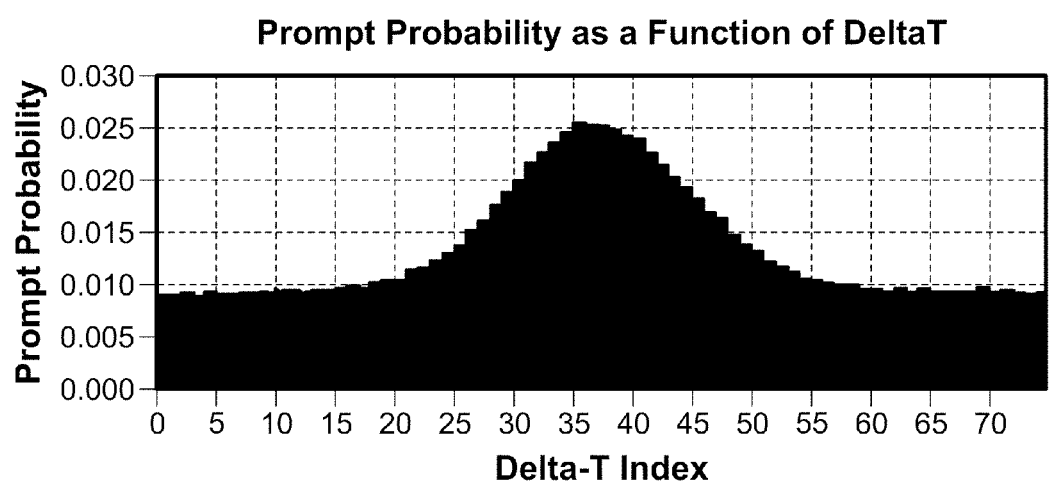
FIG. 13 is a histogram illustrating an exemplary DeltaT Distribution.
Figure 14:
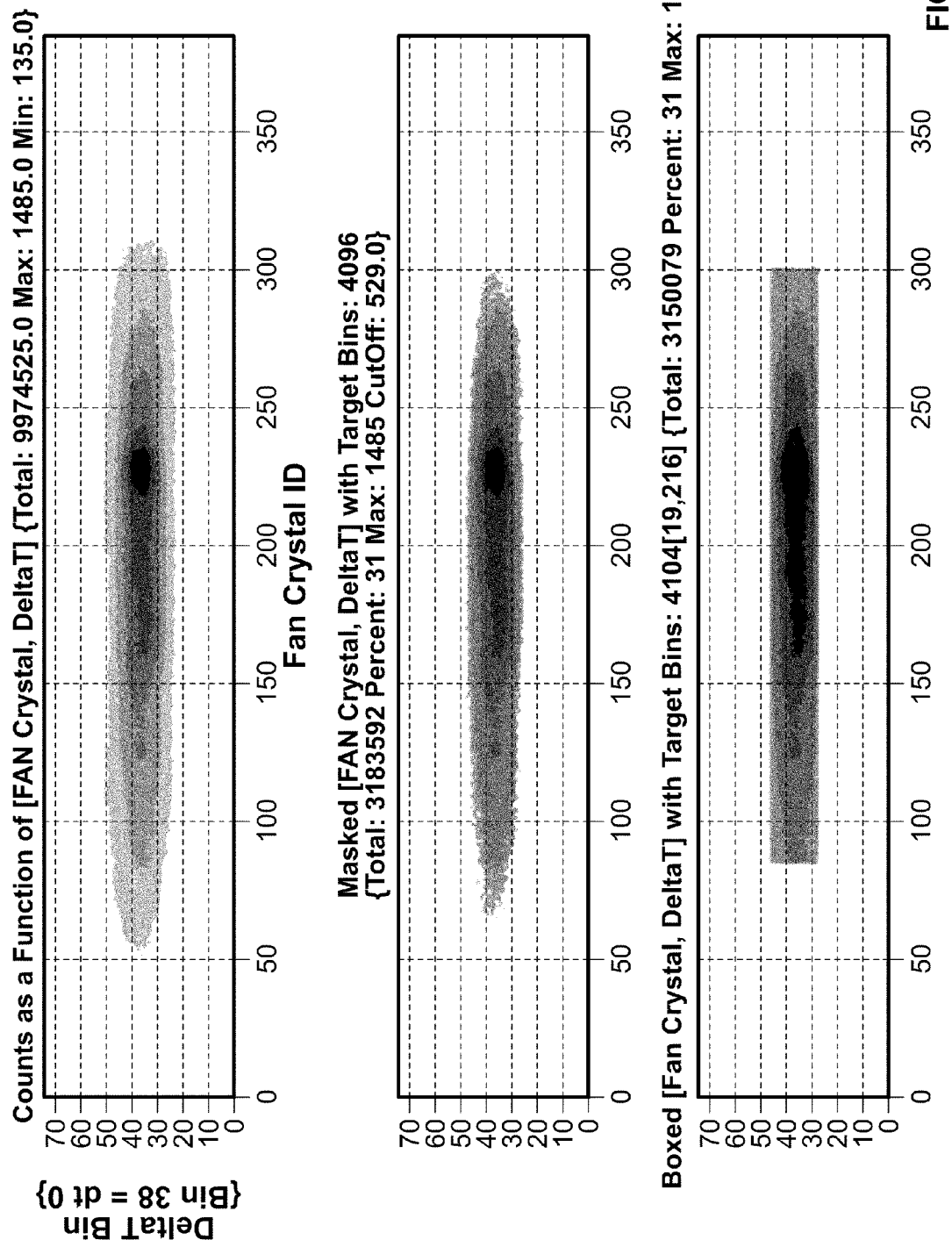
FIG. 14 is a plurality of DeltaT vs. fanCrystalID Prompt Histograms.

For example, FIG. 13 illustrates the histogram of DeltaT Distribution DeltaT values associated with the Prompts of the selected exemplary imaging system 10. Due to the detector ring geometry, and centering of the patient in the FOV of the scanner, event deltaT values are more likely to be small rather than large. In operation, the each deltaT and fanCrystalID pair are recorded as an encoded singular entity. Combining the deltaT and fanCrystalID information reduces the required encoding bits by one bit per event. In the exemplary embodiment, from 16 (7 for deltaT+9 for fanCrystalID) to 15 for dtFanPair. As a result, the favorable probability relationship associated with deltaT, fanCrystalID pairs is leveraged to compress the exemplary stream of data 106. FIG. 14 is a plurality of DeltaT vs. fanCrystalID Prompt Histograms. More specifically during operation the dtFanPairId is used for identifying the more likely occurring prompt events in a PET coincidence stream.

For example, FIG. 14A illustrates the DeltaT vs. fanCrystalID Prompt Histogram of prompts for a sub-list of the selected exemplary list. FIG. 14B illustrates the largest DeltaT-FanCrystal Pair Histogram. Specifically, FIG. 14B illustrates the 8192 cells (pixels) that have the largest counts in the histogram. Pixels of the original histogram were zeroed if they did not belong to the set of 8192 pixels with the largest counts. FIG. 14C illustrates DeltaT-FanCrystal Pair Counts In Simple Box Map More specifically FIG. 14B illustrates a subset of the pixel counts where a simple exclusion rule is applied, i.e. excluding (zeroing) the pixel counts on the outer rows and columns of the image. Overall, FIG. 14 illustrates a simple dtFanPair Id assignment rule where the more likely occurring events in the center of the box can be assigned Ids 0-8191 (and encoded in 13 bits).

At step 212 there is therefore generated an IEvent table:

| IEvent |
|---|
| RingPairID |
| TraxID |
| dtFanPairID |

The IEvent table includes fewer numbers or identifiers than are typically used to identify the prompt 300 and therefore illustrated an exemplary method for compressing the data stream. For example, assuming that the exemplary data stream 106 includes millions of prompts, reducing the quantity of information that is associated with each prompt, while still maintaining sufficient information to perform image reconstruction, reduces the overall size of the file. In another embodiment, the IEvent table may also include additional information such as, for example, measured Energies for the two gamma rays, depth of interaction, Delay vs Prompt indicator, etc.

The method 200 further includes determining if a prompt, such as prompt 300 is of a predetermined type. In the exemplary embodiment, the prompts are assigned as either a Type A or a Type B prompt based on a predetermined probability criteria. More specifically the Type A and Type B events are defined in accordance faith the following equations:

Type A: the event has a traxID<128 and a dtFanPairID<8192

Type B: the event has a traxID>=128 or a dtFanPairID>=8192

Although the exemplary embodiment illustrates only two types of event classification, e.g. Type A and Type B, it should be realized that three or more types of classification may be included based on the detector geometry of the system implementing the methods herein. In the exemplary embodiment the prompts are classified as Type A or Type B based on their probability of occurrence using event subfield information such as the delta TOF, fan crystal, and/or transaxial ID of each detected event. Optionally, the prompts may be classified using the measured energy of each prompt or Delay vs Prompt indicator, for example, if the prompt definition includes the additional information. Moreover, context sensitive classifications of Prompts into groups based on probability of occurrence may be utilized. For example, a set of rules tuned for Head/Brain Studies vs. Whole Body Oncology. Note: for Brain versus whole body studies different weights may be applied to deltaT and fan crystal numbers for Type A versus Type B event classification.

In the exemplary embodiment the percentage of Type A events is 26% based on a probability of a prompt having a traxID less than 128 and a 0.48 probability of the prompt originating from a dtFanPair ID that is less than 8192 when using a dtFanPairID look-up table. In use, Type A events occur more frequently and are therefore stored using a first quantity of bits. Whereas, the Type B events occur less frequently and therefore are stored using a second quantity of bits that is larger than the first quantity of bits used to store the Type A events. It should be realized that these percentages and probabilities are exemplary only, and will vary based on the selected event probability classification rules, and the specific detector and imaging system utilizing the exemplary method. Optionally and as stated previously, the prompts may be re-ordered based on subfields other than RingPair, such as the prompts may be re-ordered based on the theta angle. For example, the prompts may be re-ordered using the radial components of the prompt, the delta TOF of the prompt, or the detected energy of the prompt.

At step 222, the IEvent generated for prompt 300 is binned or ordered based on the RingPairID number. Assuming that the exemplary detector 40 includes 600 crystals, the prompts are binned into 600 separate bins based on the RingPairID number and whether the prompt is a Type A or Type B prompt. More specifically referring again to Table 2 shown in FIG. 7, each bin is assigned to a specified RingPairID number. For example, assuming that prompt 300 is assigned a RingPairID number of 65, and assuming that the prompt 300 is classified as a Type A, the IEvent data generated for prompt 300 is then stored in bin 65. Moreover, within each bin the RingPairIDs are store chronologically first and then stored by Type A or Type B within the chronological list second. As will be discussed below.

After the IEvent has been generated for prompt 300, the method 200 further includes acquiring 210 a prompt, such as prompt 302 of interstice 122 shown in FIG. 6. As discussed above, an IEvent is generated for prompt 302 and the IEvent is binned based on the RingPairID number generated using prompt 302, and whether the prompt 302 is a Type A or Type B prompt. More specifically referring again to Table 2 shown in FIG. 7, in the is example, prompt 302 has RingPairID number of 342 and is a Type B prompt, as a result, the IEvent data generated for prompt 302 is then stored in bin 342. Moreover, within each bin the RingPairIDs are stored chronologically first and then stored by Type A or Type B within the chronological list second.

In the exemplary embodiment, the interstice 122 includes N prompts or detected events that are each processed to generate an IEvent. For example, assuming that N=1000, then 1000 IEvents are generated, one for each prompt within the interstice 122. The N prompts are then binned into the 600 bins first based on the RingPairIDs and then arranged within each bin based on whether the event is a Type A or Type B event. For example, assuming that of the 1000 IEvents generated, 20 of the IEvents have a RingPairID number of 65. Moreover, assuming that of the 20 IEvents having a RingPairID number of 65, 5 are Type A and 15 are Type B, the 20 events will be stored first as Type A events followed by the Type B events. In the exemplary embodiment, the Type A or Type B events do not need to be chronologically ordered within a given Interstice and/or RingPair, but rather, for a given Ring Pair of an Interstice, the Type A events are grouped distinct from the Type B events.

Once, each prompt 104 in interstice 122 has been processed, method 200 further generating 224 a table 225, shown in FIG. 15, of counts of Type A and B prompts per RingPairID. The table 225 (shown in FIG. 7) generally indicates hows many events are in each RingPair bin and hows many events of a given RingPair are Type A events and how many are Type B events. For example, bin 65 may include 2000 events having a RingPairID of 65. Of the 2000 events, 200 may be classified as Type A events and 1800 may be classified as Type B events. A separate table 225 is generated for each interstice 120.

At step 226, the table 225 is processed and recorded in the compressed data stream for the benefit of re-assembling the prompts at decompression time. During operation, event map entries are encoded into a compressed data stream to record the quantity of Type A and Type B events per RingPair bin. For example, at step 226 another exemplary table (not shown) is generated using table 225 shown in FIG. 15. In the exemplary embodiment at step 226 the table 225 is encoded to reduce or compress the data size of the table 225 to generate an encoded table. For example, assuming that the table 225 requires X bytes to store, the table generated at step 226 requires Y bytes, wherein Y is less than X. Generally the table 225 is encoded using as few of bits as possible to encode the table. In the exemplary embodiment, the encoding scheme for encoding the Table of A, B events per RingPair is count rate adaptive in nature, i.e. changes as a function of the total prompts in the Interstice and incorporates run-length and code delta-value compression techniques. For example, in one embodiment if the count rate is low a first encoding scheme is utilized that leverages a technique that several RingPairs may not have any prompts associated with them and special codes are inserted to indicate the lack of prompts for several consecutive Ring Pairs. Optionally if the count rate is high a second encoding scheme is utilized that indicates consecutive RingPairs have at least one or more associated prompts. As discussed above, the count rate is the number of prompts per Interstice. It should be realized that the exemplary embodiment described herein is only one of multiple embodiments where a different encoding of the Table of A,B events per RingPair can be deployed. Additional examples of embodiment variation include use of a RingPair assignment that leverages subtle sensitivity variances of ring pairs. In this case, the arbitrary RingPair mapping may exploit sensitivity variances and have RingPair Ids assigned from best sensitivity to lowest sensitivity, thus increasing consecutive RingPairs without corresponding prompts at low count rates toward the end of RingPair list/table and thus facilitating run-length encoding of consecutive RingPairs without any Type A or Type B events.

At step 228, the RingPairID number is set to 0. For example, referring again to table 225 in FIG. 7, at step 228 the actual events in the table 228 are programmed into the compressed data stream. During operation, for each ring pair, the first ring pair is processed such that at step 230, the Type A's prompts are appended into the compressed data stream using the smallest bit size possible. It should be realized that since the data is sorted based on the RingPairID, the RingPairID number does not need to be appended into the compressed data stream, thus further reducing or compressing the size of the data stream. As a result, the only information that is appended into the compressed data stream is the traxID and the dtFanPairID.

At step 232, the Type B's prompts are then appended into the compressed data stream. At step 234, the RingPairID is then incremented to the next RingPairID number and the Type A and Type B events are appended into the compressed data stream as described above. This process is continued for each ring pair. For example, assuming there are 600 hundred ring pairs, at step 228 each ring pair 0-599 will be sequentially processed, and each Type A and Type B event for each ring pair will be sequentially processed into the compressed data stream.

Inserting Type A first, then Type B events into the compressed stream is arbitrary in nature. If Type B first, followed by Type A offers better performance or additional data compression benefit, then the order of insertion can be altered without significance to the processing.

At step 236 the method includes determining if all the ring pairs have been processed. If no, the RingPairID is incremented to the next sequential RingPairID number and steps 230-234 are repeated. If all the ring pairs for the interstice 122 have been processed the method proceeds to step 238. At step 238, assuming that each prompt 104 in interstice 122 has been processed, method 200 further includes appending the time marker or trigger event. As discussed above, the interstices 120 are separated by or defined between either a time marker or a physiological trigger. As such, at step 238, the method includes appending the time marker or trigger event into the compressed data stream and acquiring the next subsequent interstice 120, such as interstice 124 shown in FIG. 6. The interstice 124 is then processed the same as interstice 122 as discussed above. The method is continued at step 240 until each interstice 120 in the stream of data 106 has been processed as discussed above. At step 242 the compressed data stream is output to either the sorter 80 or may be stored as a list file in memory for future use.

The decompressing of the compressed stream or list of event data is basically a reversal of the compression processing steps, with the exception that the events are not restored to their original chronological order within the interstice's defined unit of time. Since all remapping of prompt information is done by 1:1 correspondence tables, the reversal process is deterministic and lossless in nature.

The method 200 for compressing the list data file or the stream of data may be implemented on the list files post acquisition and prior to histogramming. Optionally the method 200 may be used to compress no-longer frequently used list files to reduce the amount of space required for online storage of the list files, or may be used as a pre-processing step to decompress the list files prior to using the list files in the replay mode of operation. The method 200 may also be used reduce the amount of time archive the data, reduce the amount of archive media required, and/or to reduce the time to restore list files to the scanner. The method 200 may also be used 'on-the-fly' during the data acquisition process to reduce the amount of data that is written to the disk, and then automatically decompressed 'on-the-fly' when desired. The method 200 may also be used to reduce the required I/O bandwidth of the file system allowing more cost effective file system solutions. In the exemplary embodiment the method 200 is installed on the CPM 72 as a computer program or FPGA (Field Programmable Gate Array) implementation to reduce the required I/O bandwidth of the physical coincidence link between the CPM 72 and the sorter/histogrammer 80, and/or to allow higher coincidence event rates.

One of the beneficial aspects of the methods and apparatus described herein is its "streaming" performance. Not only does the compression scheme yield greater compression than general purpose data compression algorithms, it does so with much less computation and buffering or windowing of the data. The methods and apparatus described herein achieve high data reduction at low computational cost and require only one interstice of windowing or buffering of the data stream. And note that the interstice unit of time is arbitrary but an interstice of one millisecond results in industry leading level of data reduction, at least in the context of a PET coincidence event stream. Furthermore, the scheme leverages generalized event probability rules derived by pre-analysis of representative streams and the selected rules will be applicable for the entire duration of the list and/or stream and does not require extensive runtime analysis of the data in the stream nor does the event probability rules information have to be embedded periodically in the compressed data stream to achieve high compression.

A technical effect of the methods and apparatus described herein provides a fully automatic lossless method of compressing a stream of imaging data that facilitates improving system performance and/or reducing the system storage requirements. Some embodiments of the present invention provide a machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the monitor or display or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the tapes of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for compressing imaging data using a computer comprising:
    acquiring a stream of imaging data;
    dividing the stream of imaging data into a plurality of interstices, each interstice including a plurality of detected events;
    classifying the detected events within each interstice based on a probability of occurrence of the detected event; and
    re-ordering the detected events within each interstice based on the probability of occurrence to compress the image data.

2. A method in accordance with claim 1 further comprising re-ordering the detected events based on at least one of a ring pair identification number and a derived transaxial angle.

3. The method in accordance with claim 1 wherein acquiring a stream of imaging data further comprises acquiring a stream of Positron Emission Tomography (PET) imaging data, the PET imaging data includes a plurality of interstices, each interstice includes a plurality of detected events.

4. The method in accordance with claim 1 wherein acquiring a stream of imaging data further comprises acquiring a stream of imaging data that includes at least one of a single photon detected event and a single gamma detected event.

5. The method in accordance with claim 1 wherein dividing the stream of imaging data into a plurality of interstices further comprises dividing the stream of imaging data into a plurality of interstices using at least one of a time marker and a physiological marker.

6. The method in accordance with claim 1 further comprising:
    generating an IEvent for each detected event, wherein the IEvent includes at least a RingPairID number, a TraxID number, and a dtFanPairID number; and
    binning each IEvent generated based on the RingPairID number.

7. The method in accordance with claim 6 further comprising:
    determining a ring pair identification number for each detected event;
    assigning each respective detected event to a ring pair bin based on the ring pair number;
    classifying each detected event in each bin based on the probability of occurrence of the detected event; and
    re-ordering the detected events within each bin based on the probability of occurrence to compress the image data.

8. The method in accordance with claim 7 further comprising:
    generating a table that indicates the quantity of detected events assigned to each respective ring pair bin and the quantity of detected events based on the classification; and
    using a count rate adaptive encode compression algorithm on the generated table to generate a compressed data stream, the count rate adaptive compression algorithm changes as a function of the total prompts in the interstice and incorporates rim-length and code delta-value compression techniques.

9. A method in accordance with claim 1, wherein classifying the detected events further comprises classifying the detected events within each interstice based on a generalization of prior analyzed event streams, wherein the prior analyzed events streams include a brain study event stream and a whole-body event stream.

10. A medical imaging system comprising:
a detector array; and
a computer operationally coupled to the detector array wherein the computer is programmed to:
acquire a stream of imaging data;
divide the stream of imaging data into a plurality of interstices, each interstice including a plurality of detected events;
classify the detected events within each interstice based on a probability of occurrence of the detected events; and
re-order the detected events within each interstice based on the probability of occurrence to generate lossless compressed image data.

11. A medical imaging system in accordance with claim 10, wherein said detector array comprises a Positron Emission Tomography (PET) detector, said stream of imaging data comprises a stream of PET imaging data, and said computer comprises a coincidence processor module.

12. A medical imaging system in accordance with claim 10 wherein said computer if further programmed to generate a ring pair identification number for each detected event in the plurality of interstices.

13. A medical imaging system in accordance with claim 10 wherein said computer if further programmed to divide the stream of imaging data into a plurality of interstices using at least one of a time marker and a physiological marker.

14. A medical imaging system in accordance with claim 10 wherein each detected event includes a first crystal axial identification and a second crystal axial identification, the computer is further programmed to assign a ring pair identification number to each detected event based on the first and second axial identifications.

15. A medical imaging system in accordance with claim 10 wherein said computer is further programmed to:
determine a ring pair identification number for each detected event;
assign each respective detected event to a ring pair bin based on the ring pair number;
classify each detected event in each bin based on the probability of occurrence of the detected events; and
re-order the detected events within each bin based on the probability of occurrence to compress the image data.

16. A medical imaging system in accordance with claim 10 wherein said computer is further programmed to:
generate a table that indicates the quantity of detected events assigned to each respective ring pair bin and the quantity of detected events based on the classification; and
use a count rate adaptive encode compression algorithm on the generated table to generate a compressed data stream, the count rate adaptive compression algorithm changes as a function of the total prompts in the interstice and incorporates run-length and code delta-value compression techniques.

17. A computer readable medium encoded with a program programmed to instruct a computer to:
acquire a stream of imaging data;
divide the stream of imaging data into a plurality of interstices, each interstice including a plurality of detected events;
classify the detected events within each interstice based on a probability of occurrence of the detected event; and
re-order the detected events within each interstice based on the probability of occurrence to compress the image data.

18. A computer readable medium in accordance with claim 17, said computer readable medium is further programmed to instruct a computer to divide the stream of imaging data into a plurality of interstices using at least one of a time marker and a physiological marker.

19. A computer readable medium in accordance with claim 17, said computer readable medium is further programmed to instruct a computer to:
determine a ring pair identification number for each detected event;
assign each respective detected event to a ring pair bin based on the ring pair number;
classify each detected event in each bin based on the probability of occurrence of the detected event; and
re-order the detected events within each bin based on the probability of occurrence to compress the image data.

20. A computer readable medium in accordance with claim 17, said computer readable medium is further programmed to instruct a computer to:
generate a table that indicates the quantity of detected events assigned to each respective ring pair bin and the quantity of detected events based on the classification; and
use a count rate adaptive encode compression algorithm on the generated table to generate a compressed data stream, the count rate adaptive compression algorithm changes as a function of the total prompts in the interstice and incorporates run-length and code delta-value compression techniques.

* * * * *